(12) United States Patent
Lee et al.

(10) Patent No.: US 11,801,318 B2
(45) Date of Patent: Oct. 31, 2023

(54) UV STERILIZATION SYSTEM FOR VEHICLE

(71) Applicants: HYUNDAI MOTOR COMPANY, Seoul (KR); KIA MOTORS CORPORATION, Seoul (KR); KAIS Inc., Pyeongtaek-si (KR)

(72) Inventors: Jaeseung Lee, Hwaseong-si (KR); Younghoon Ji, Osan-si (KR)

(73) Assignees: HYUNDAI MOTOR COMPANY, Seoul (KR); KIA MOTORS CORPORATION, Seoul (KR); KAIS Inc., Pyeongtaek-si (KR)

( * ) Notice: Subject to any disclaimer, the term of this patent is extended or adjusted under 35 U.S.C. 154(b) by 303 days.

(21) Appl. No.: 17/204,433

(22) Filed: Mar. 17, 2021

(65) Prior Publication Data

US 2022/0080064 A1    Mar. 17, 2022

(30) Foreign Application Priority Data

Sep. 11, 2020  (KR) ......................... 10-2020-0116520

(51) Int. Cl.
*A61L 2/10*   (2006.01)
*A61L 2/26*   (2006.01)
*B60R 15/00*  (2006.01)

(52) U.S. Cl.
CPC .................. *A61L 2/10* (2013.01); *A61L 2/26* (2013.01); *B60R 15/00* (2013.01); *A61L 2202/11* (2013.01); *A61L 2202/121* (2013.01); *A61L 2202/122* (2013.01); *A61L 2202/14* (2013.01)

(58) Field of Classification Search
CPC .......... A61L 2/10; A61L 2/26; A61L 2202/11; A61L 2202/121; A61L 2202/14; B60R 5/10
See application file for complete search history.

(56) References Cited

U.S. PATENT DOCUMENTS

2020/0307472 A1* 10/2020 Line ..................... B60R 15/00
2021/0187140 A1*  6/2021 Spazier ................... B60S 1/64

* cited by examiner

*Primary Examiner* — Nicole M Ippolito
(74) *Attorney, Agent, or Firm* — LEMPIA SUMMERFIELD KATZ LLC (57) ABSTRACT

A UV sterilization system for a vehicle includes a sterilization housing in which a sterilizing object is accommodated, an LED module emitting ultraviolet rays to the sterilizing object, and a controller configured to control an operation of the LED module.

12 Claims, 9 Drawing Sheets

UV STERILIZATION SYSTEM FOR VEHICLE

CROSS-REFERENCE TO RELATED APPLICATION

This application claims priority to and the benefit of Korean Patent Application No. 10-2020-0116520, filed on Sep. 11, 2020, the entire contents of which are incorporated herein by reference.

FIELD

The present disclosure relates to an UV sterilization system for a vehicle.

BACKGROUND

The statements in this section merely provide background information related to the present disclosure and may not constitute prior art.

Some of the belongings of vehicle occupants are contaminated with bacteria, etc.

For example, there are cases where more bacteria or bacteria inhabit the belongings of a vehicle occupant, such as a mobile phone or a vehicle key, than a toilet.

When the belongings of the vehicle or occupant are contaminated with bacteria, the probability of infection with the vehicle occupant is increased through this, and accordingly, contamination can be expanded to a large area.

By using UV, particularly UV-C, more than 99.9% of bacteria can be removed, so a method using UV as a method to sterilize bacteria in a vehicle is being researched.

The above information disclosed in this Background section is only for enhancement of understanding of the background of the disclosure, and therefore it may contain information that does not form the prior art that is already known to a person of ordinary skill in the art.

SUMMARY

The present disclosure provides a vehicle UV sterilization system capable of sterilizing belongings such as mobile phones.

A UV sterilization system for a vehicle according to one form of the present disclosure may include a sterilization housing in which a sterilizing object is accommodated, an LED module emitting ultraviolet rays to the sterilizing object, and a controller configured to control an operation of the LED module.

The UV sterilization system may further include an upper reflector that reflects the ultraviolet rays emitted from the LED module to the sterilizing object.

The upper reflector may include a plurality of reflecting plates configured to reflect the ultraviolet rays emitted from the LED module to the sterilizing object.

The plurality of reflecting plate may include a coating layer of a material containing aluminum.

The UV sterilization system may further include a lower LED module emitting ultraviolet rays to the bottom of the sterilizing object.

The UV sterilization system may further include a lower reflector that reflects the ultraviolet rays emitted from the lower LED module to the sterilizing object.

The lower reflector may include a plurality of reflecting plates configured to reflect the ultraviolet rays emitted from the LED module to bottom of the sterilizing object.

The plurality of reflecting plate may include a coating layer of a material containing aluminum.

The UV sterilization system may further include at least one sensor configured to detect the sterilizing object and output a corresponding signal, the lower LED module may be provided in plural, and the controller may be configured to operate the lower LED module corresponding to the sensor that detects the sterilizing object among the at least one sensor.

The UV sterilization system may further include a moving module configured to move the lower LED module in one direction, and at least one sensor configured to detect the sterilizing object and output a corresponding signal, and the lower LED module may be provided in plural, and the controller may be configured to operate the lower LED module corresponding to the sensor that detects the sterilizing object among the at least one sensor.

The UV sterilization system may further include a charger mounted on the sterilization housing.

The UV sterilization system may further include a housing cover covering the sterilization housing.

According to the UV sterilization system for a vehicle according to one form of the present disclosure, it may be possible to sterilize belongings such as mobile phones.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In the drawings, the thickness of layers, films, panels, regions, etc., are exaggerated for clarity.

When a part such as a layer, film, region, or plate is said to be "on" another part, this includes not only the case directly above the other part, but also the case where there is another part in between.

In contrast, when an element is referred to as being "directly on" another element, there are no intervening elements present.

Throughout the specification, when a part "includes" a certain component, it means that other components may be further included rather than excluding other components unless specifically stated to the contrary.

One form of the present disclosure will hereinafter be described in detail with reference to the accompanying drawings.

Figure 1:
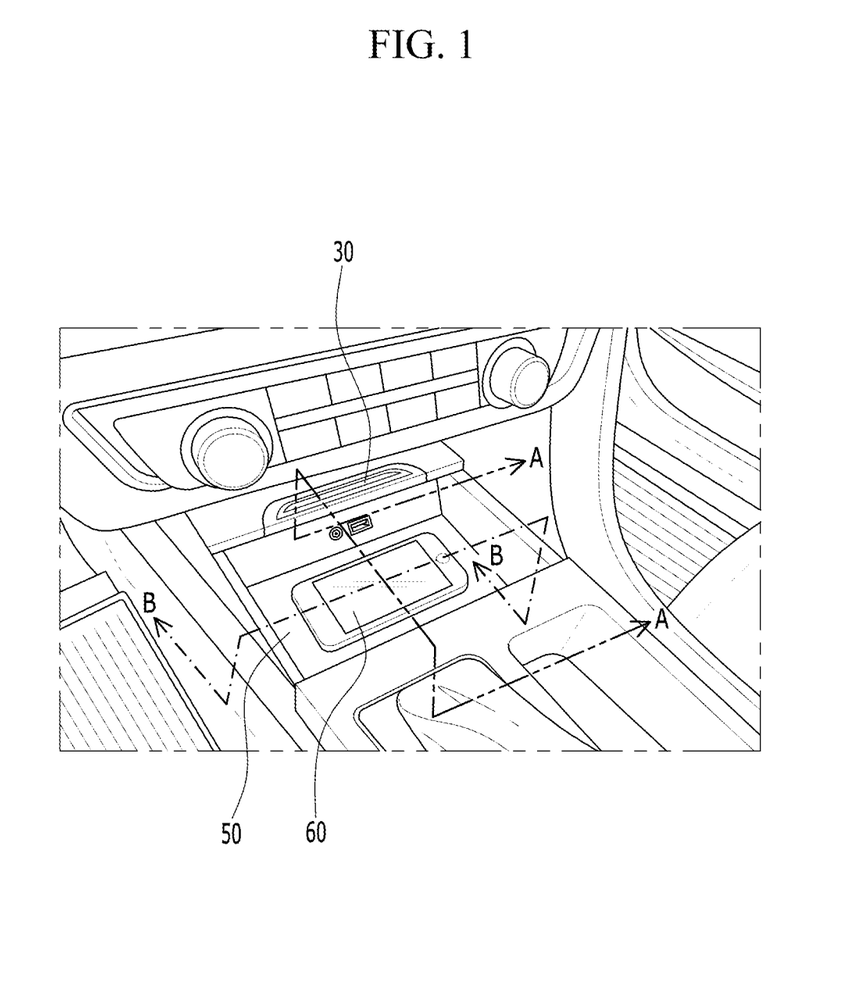
FIG. 1 is a perspective view of a UV sterilization system for a vehicle according to one form of the present disclosure.

FIG. 1 is a perspective view of a UV sterilization system for a vehicle according to one form of the present disclosure.

Referring to FIG. 1, a UV sterilization system for a vehicle according to one form of the present disclosure may be mounted in a space between a center fascia and a console box of a vehicle, so that easy access of a driver may be possible. However, the mount position of the UV sterilization system for a vehicle according to one form of the present disclosure is not limited thereto, and a position that is easily accessible to occupants other than the driver, for example, a rear of the console box or a rear of the seat. That is, it can be mounted in various positions.

Figure 2:
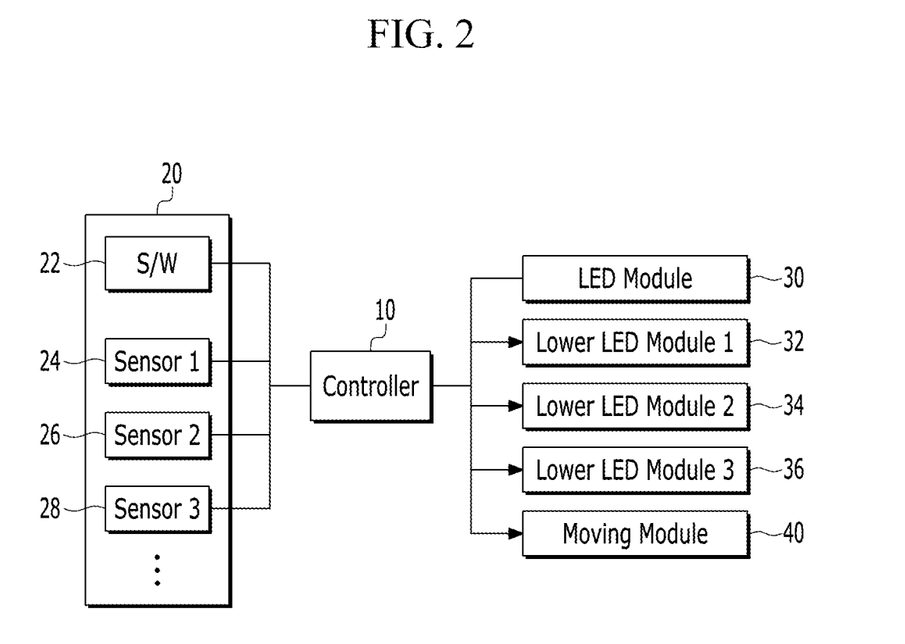
FIG. 2 is a schematic diagram of a UV sterilization system for a vehicle according to one form of the present disclosure.

FIG. 2 is a schematic diagram of a UV sterilization system for a vehicle according to one form of the present disclosure.

Referring to FIG. 1 and FIG. 2, a UV sterilization system for a vehicle according to one form of the present disclosure may include a sterilization housing 50 in which an object 60 to be sterilized (a sterilizing object) is accommodated, an LED module 30 that emits ultraviolet rays through the sterilizing object 60, and a controller 10 that is configured to control the operation of the LED module 30.

The LED module 30 may include, for example, an LED lamp that emits UV (ultraviolet rays) and a printed circuit board (PCB). The LED module 30 can perform the sterilization of the sterilizing object 60 (the object to be sterilized 60) by emitting ultraviolet rays, particularly the UVC wavelength with excellent sterilization effect.

The UV sterilization system for a vehicle according to one form of the present disclosure further includes a state measurement unit 20 including a switch 22 for ON/OFF operation of the LED module and at least one sensor 24, 26, 28 to be described later. And, according to the output signal of the state measurement unit 20, the controller 10 can control the operation of the LED module 30 and lower LED modules 32, 34, 36 and moving module 40 to be described later.

Figure 3:
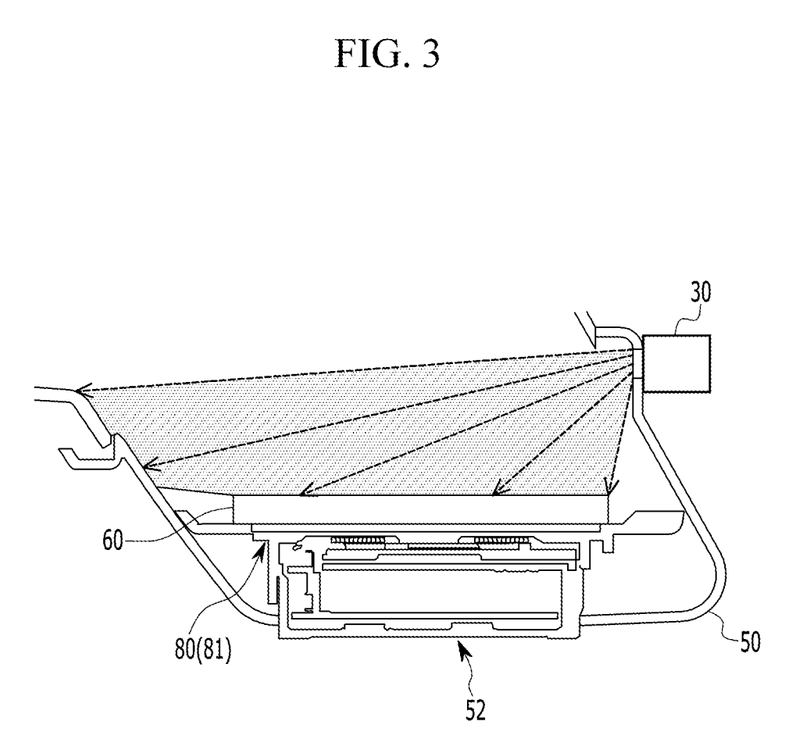
FIG. 3 is a cross-sectional view along line A-A in FIG. 1.

FIG. 3 is a cross-sectional view along line A-A in FIG. 1.

Referring to FIG. 3, the UV sterilization system for a vehicle according to one form of the present disclosure may further include a charger 52 mounted on the sterilization housing 50.

For example, the sterilizing object 60 may be a mobile phone, and the charger 52 is mounted on the sterilization housing 50 to simultaneously charge and sterilize the mobile phone 60.

The charger 52 can be a wired or wireless charger.

The sterilizing object 60 may be a driver's or a passenger's belongings, and may include various types of belongings, such as a vehicle key and a wallet.

Figure 4:
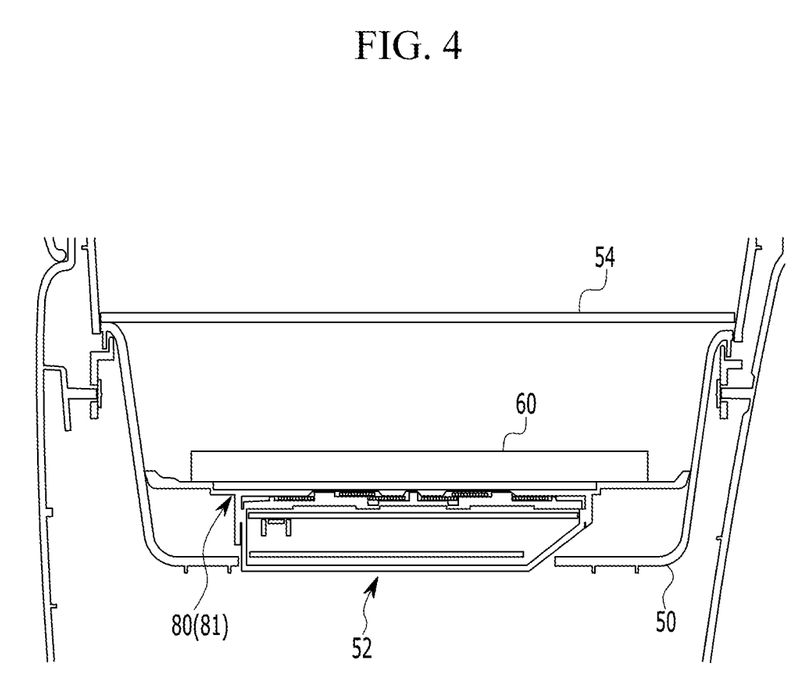
FIG. 4 is a cross-sectional view along line B-B in FIG. 1.

FIG. 4 is a cross-sectional view along line B-B in FIG. 1.

The UV sterilization system for a vehicle according to one form of the present disclosure may further include a housing cover 54 covering the sterilization housing 50.

The ultraviolet rays emitted from the LED module 30 can be fatal to the human skin and eyes, and the housing cover 54 inhibits the ultraviolet rays from leaking into the vehicle to protect the driver and occupant.

Figure 5:
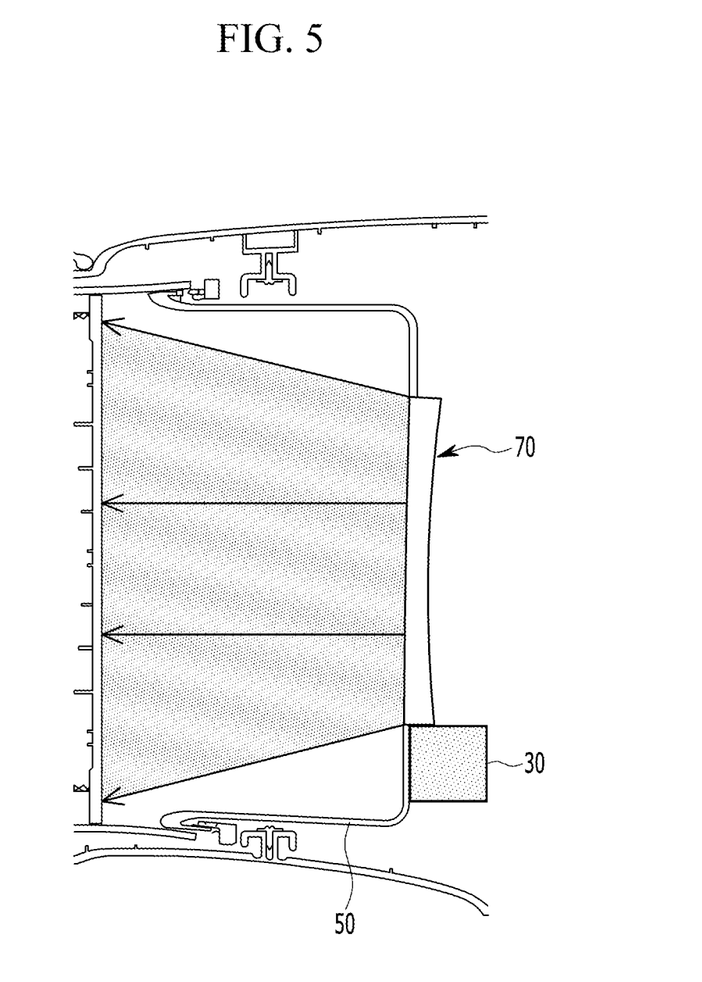
FIG. 5 is a top plan view of a UV sterilization system for a vehicle according to one form of the present disclosure.
Figure 6:
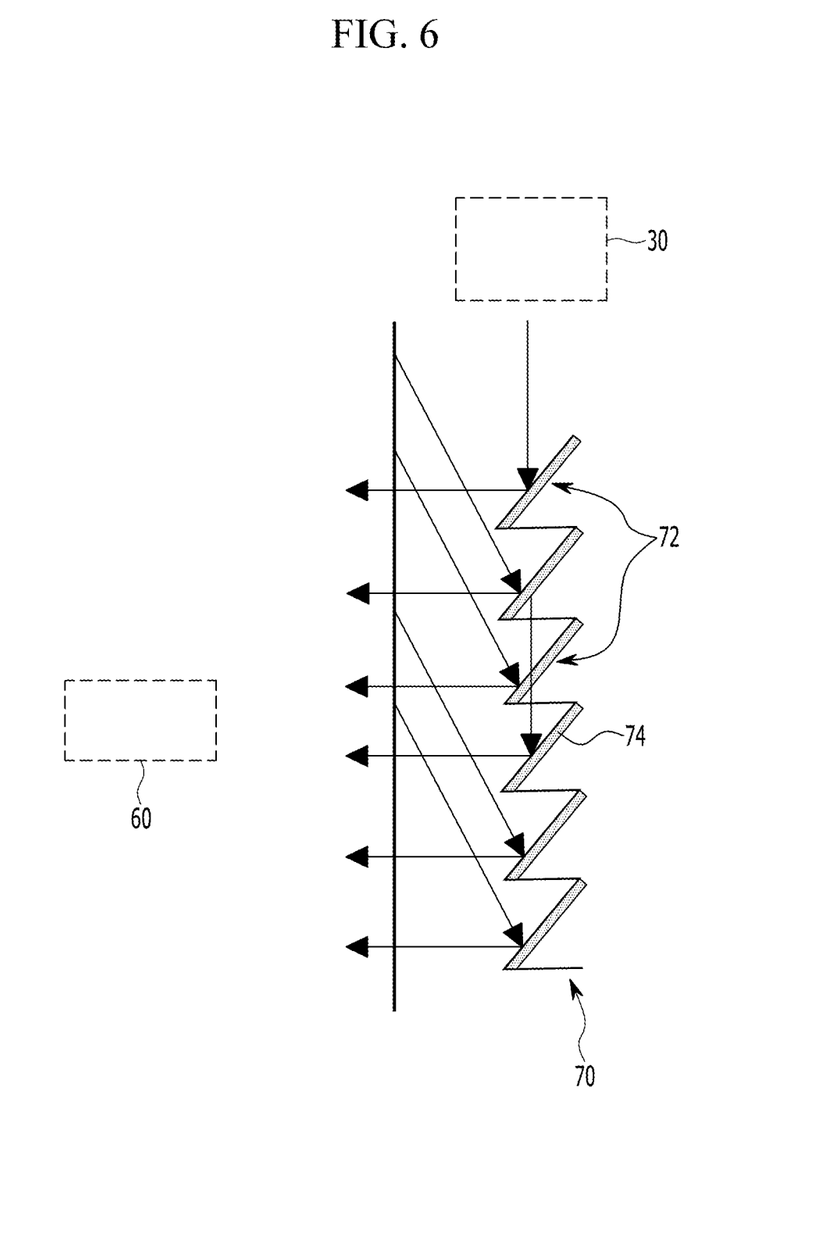
FIG. 6 is a cross-sectional view of an upper reflector of a UV sterilization system for a vehicle according to one form of the present disclosure.

FIG. 5 is a top plan view of a UV sterilization system for a vehicle according to one form of the present disclosure, and FIG. 6 is a cross-sectional view of an upper reflector of a UV sterilization system for a vehicle according to one form of the present disclosure.

Referring to FIG. 5 and FIG. 6, the UV sterilization system for a vehicle according to one form of the present disclosure may further include an upper reflector 70 that reflects the ultraviolet rays emitted from the LED module 30 to the sterilizing object 60.

The upper reflector 70 may include a plurality of reflecting plates 72 configured to reflect the ultraviolet rays emitted from the LED module 30 to the sterilizing object 60. The plurality of reflecting plates 72 may be inclined to reflect the direct or reflected ultraviolet rays of the LED module 30 to the sterilization object 60.

The plurality of reflecting plates 72 may include a coating layer 74 of a material including aluminum. The coating layer 74 of a material containing aluminum can effectively reflect UVC (Ultraviolet-C; short-wave ultraviolet rays) to increase the sterilization effect.

Figure 7:
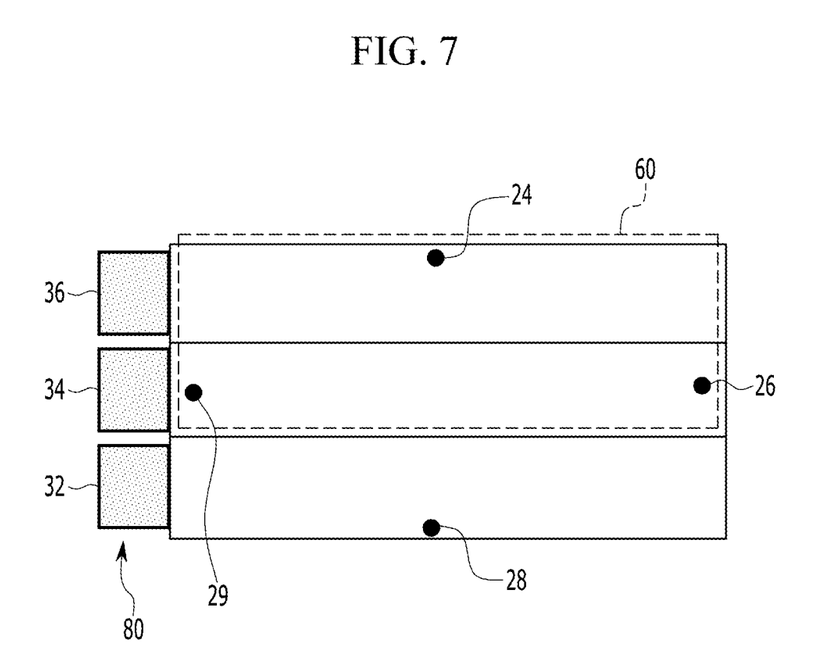
FIG. 7 is a top plan view of the lower sterilization unit of the UV sterilization system for a vehicle according to one form of the present disclosure.
Figure 8:
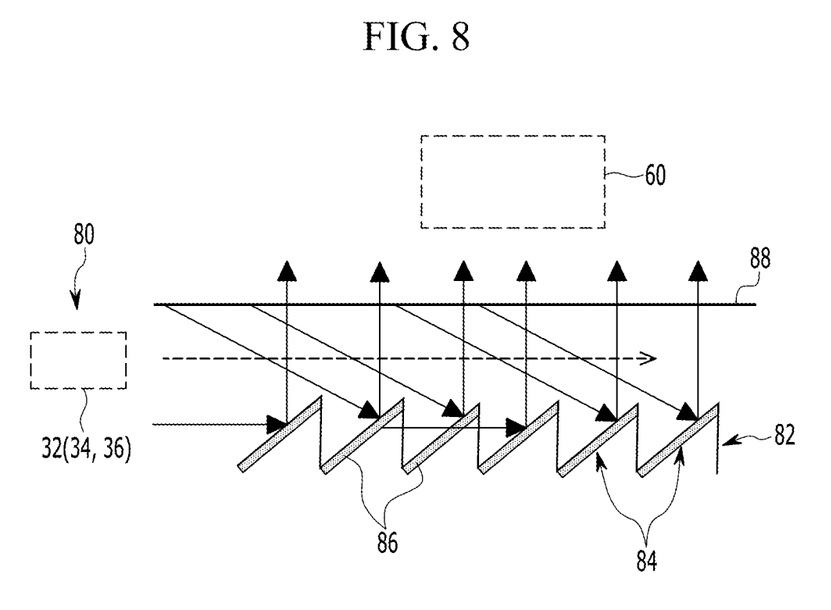
FIG. 8 is a cross-sectional view of a lower reflector of a UV sterilization system for a vehicle according to one form of the present disclosure.

FIG. 7 is a top plan view of the lower sterilization unit of the UV sterilization system for a vehicle according to one form of the present disclosure, and FIG. 8 is a cross-sectional view of a lower reflector of a UV sterilization system for a vehicle according to one form of the present disclosure.

Referring to FIG. 3, FIG. 4, FIG. 7 and FIG. 8, The UV sterilization system for a vehicle according to one form of the present disclosure may further include a lower LED module 80 that emits ultraviolet rays under the sterilizing object 60.

Like the LED module 30 described above, the lower LED module 80 may include, for example, an LED lamp that emits UV (ultraviolet rays) and a printed circuit board (PCB). The lower LED module 80 can sterilize the lower part of the sterilizing object 60 by emitting ultraviolet rays, particularly the UVC wavelength with excellent sterilization effect.

In addition, the UV sterilization system for a vehicle according to one form of the present disclosure may further include a lower reflector 82 that reflects the ultraviolet rays emitted from the lower LED module 80 to the sterilizing object 60.

The lower reflector 82 may include a plurality of reflecting plate 84 configured to reflect the ultraviolet rays emitted from the lower LED module 80 to the bottom of the sterilizing object 60, and the plurality of reflecting plates 84 may include a coating layer 86 of a material containing aluminum.

The plurality of reflecting plates 84 may be inclined to reflect the direct or reflected ultraviolet rays of the lower LED module 80 to the sterilizing object 60. And the coating layer 86 of the material containing aluminum can effectively reflect UVC (Ultraviolet-C; short-wave ultraviolet rays) to increase the sterilization effect.

The UV sterilization system for a vehicle according to one form of the present disclosure may further include a support plate 88 supporting the sterilizing object 60, and the support plate 88 is a material capable of transmitting ultraviolet rays. For example, it can be made of transparent plastic or tempered glass.

Referring to FIG. 2 and FIG. 7, the UV sterilization system for a vehicle according to one form of the present disclosure may further include at least one sensor 22, 24, 26, 29 that senses the sterilizing object 60 and outputs a corresponding signal. In addition, the lower LED module 80 may be provided in a plurality 32, 34, 36. And the controller 10 can operate the lower LED modules 32, 34, 36 corresponding to the sensor that detected the sterilizing object 60 among the at least one sensors 22, 24, 26, 29.

For example, when some sensors 24, 26, 29 detect the sterilizing object 60, the controller can operate only some lower LED modules 34, 36 as shown in FIG. 7 and FIG. 8.

The sensors 22, 24, 26, 29 may be an infrared sensor, for example, but is not limited thereto.

The ultraviolet rays emitted from the lower LED module 80 can be fatal to the skin and eyes of the human body. Particularly the ultraviolet rays emitted from the lower part can be irradiated to the eyeballs such as drivers. By operating only the lower LED module corresponding to the detected sensor, it is possible to protect the driver and occupant by inhibiting ultraviolet rays from leaking into the vehicle.

Figure 9:
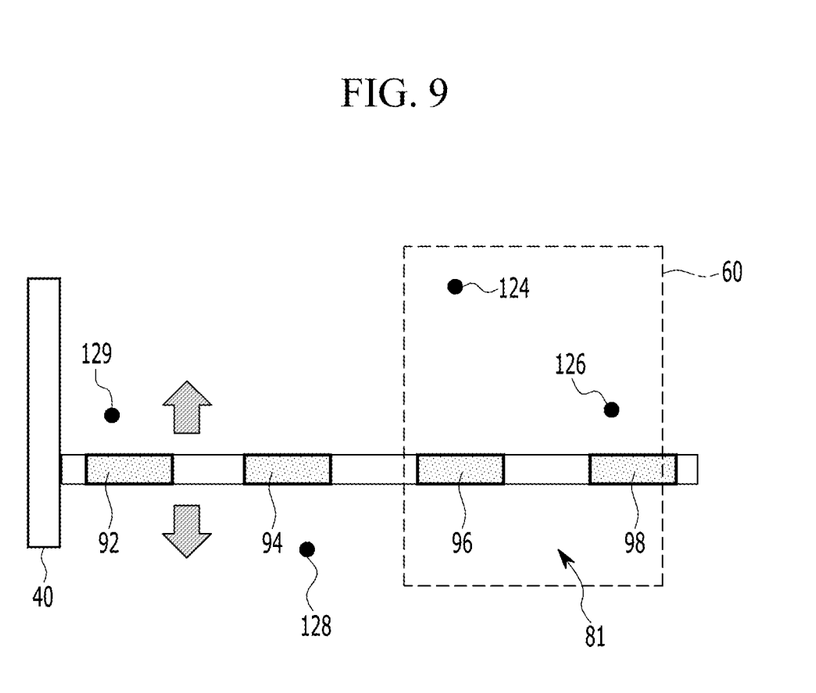
FIG. 9 is a top plan view of the lower sterilization unit of the UV sterilization system for a vehicle according to another form of the present disclosure.

FIG. 9 is a top plan view of the lower sterilization unit of the UV sterilization system for a vehicle according to another form of the present disclosure.

For ease of understanding, in describing the UV sterilization system for a vehicle illustrated in FIG. 9, a repeated description of the vehicle UV sterilization system according to one form of the present disclosure described in FIG. 1 to FIG. 6 will be omitted.

Referring to FIG. 3, FIG. 4 and FIG. 9, the UV sterilization system for a vehicle according to one form of the present disclosure may further include a moving module 40 configured to move the lower LED module 81 in one direction, and the lower LED module 81 may be provided in plurality 92, 94, 96, 98.

The moving module 40 may include, for example, a configuration for driving a motor or actuator, and a rail guiding the movement of the plurality of lower LED modules 92, 94, 96, 98, etc. The moving module 40 can be operated by the control of the controller 10. The configuration of the moving module 40 and the control of the controller 10 are obvious to a person skilled in the art, and a detailed description thereof will be omitted.

The UV sterilization system for a vehicle according to one form of the present disclosure further includes at least one sensor 124, 126, 128, 129 that detects the sterilizing object 60 and outputs a corresponding signal. And the controller operates the lower LED module 92, 94, 96, 98 corresponding to the sensor 124, 126, 128, 129 that detects the sterilizing object 60 among one sensor 124, 126, 128, and 129.

As shown in FIG. 9, for example, by operating only the lower LED modules 96, 98 corresponding to sensors 124, 126 that detect the sterilizing object 60, it is possible to inhibit leakage of ultraviolet rays.

As described above, according to the UV sterilization system for a vehicle according to one form of the present disclosure, sterilization of belongings such as a mobile phone may be possible.

In addition, according to the UV sterilization system for a vehicle according to one form of the present disclosure, when the charger is mounted, charging of the mobile phone and sterilization of the charger are possible simultaneously.

While this disclosure has been described in connection with what is presently considered to be practical exemplary forms, it is to be understood that the disclosure is not limited to the disclosed forms. On the contrary, it is intended to cover various modifications and equivalent arrangements included within the spirit and scope of the appended claims.

DESCRIPTION OF SYMBOLS

| | |
|---|---|
| 10: controller | 20: state measurement unit |
| 22: switch | 24-29: sensor |
| 30: LED module | 32-36: lower LED module |
| 40: moving module | 50: sterilization housing |
| 52: charger | 54: cover |
| 60: sterilizing object | 70: upper reflector |
| 72: reflecting plate | 74: coating layer |
| 80, 81: lower sterilization unit | 82: lower reflector |
| 84: reflecting plate | 86: coating layer |
| 88: support plate | 92-96: lower LED module |
| 124-129: sensor | |

What is claimed is:

1. A UV sterilization system for a vehicle, the UV sterilization system comprising:
    a sterilization housing in which a sterilizing object is accommodated;
    an LED module and a plurality of lower LED modules configured to emit ultraviolet rays to the sterilizing object;
    a controller configured to control a lower LED module, among the plurality of lower LED modules, corresponding to a sensor that detects the sterilizing object among at least one sensor.

2. The UV sterilization system of claim 1, further comprising an upper reflector configured to reflect the ultraviolet rays emitted from the LED module to the sterilizing object.

3. The UV sterilization system of claim 2, wherein the upper reflector comprises a plurality of reflecting plates.

4. The UV sterilization system of claim 3, wherein the plurality of reflecting plate includes a coating layer containing aluminum.

5. The UV sterilization system of claim 1, wherein the plurality of lower LED modules configured to emit the ultraviolet rays to a bottom of the sterilizing object.

6. The UV sterilization system of claim 5, further comprising a lower reflector configured to reflect the ultraviolet rays emitted from the plurality of lower LED modules to the sterilizing object.

7. The UV sterilization system of claim 6, wherein the lower reflector comprises a plurality of reflecting plates.

8. The UV sterilization system of claim 7, wherein the plurality of reflecting plate includes a coating layer containing aluminum.

9. A UV sterilization system for a vehicle, the UV sterilization system comprising:
    a sterilization housing in which a sterilizing object is accommodated;
    an LED module configured to emit ultraviolet rays to the sterilizing object;
    a controller configured to control an operation of the LED module;
    at least one lower LED module configured to emit ultraviolet rays to a bottom of the sterilizing object;
    a lower reflector configured to reflect the ultraviolet rays emitted from the at least one lower LED module to the sterilizing object; and signal, at least one sensor configured to detect the sterilizing object and output a corresponding signal,
wherein the at least one lower LED module includes a plurality of lower LED modules,
wherein each lower LED module of the plurality of lower LED modules corresponds to each sensor of at least one sensor, and
wherein the controller is configured to operate a lower LED module, among the plurality of lower LED modules, corresponding to a sensor that detects the sterilizing object among the at least one sensor.

10. A UV sterilization system for a vehicle, the UV sterilization system comprising:
a sterilization housing in which a sterilizing object is accommodated;
an LED module configured to emit ultraviolet rays to the sterilizing object;
a controller configured to control an operation of the LED module;
at least one lower LED module configured to emit ultraviolet rays to a bottom of the sterilizing object;
a moving module configured to move the at least one lower LED module in one direction; and
at least one sensor configured to detect the sterilizing object and output a corresponding signal,
wherein the at least one lower LED module includes a plurality of lower LED modules,
wherein each lower LED module of the plurality of lower LED modules corresponds to each sensor of at least one sensor, and
wherein the controller is configured to operate a lower LED module, among the plurality of lower LED modules, corresponding to a sensor that detects the sterilizing object among the at least one sensor.

11. The UV sterilization system of claim 1, further comprising:
a charger mounted on the sterilization housing.

12. The UV sterilization system of claim 1, further comprising:
a housing cover covering the sterilization housing.

* * * * *

UNITED STATES PATENT AND TRADEMARK OFFICE
CERTIFICATE OF CORRECTION

PATENT NO. : 11,801,318 B2
APPLICATION NO. : 17/204433
DATED : October 31, 2023
INVENTOR(S) : Jaeseung Lee et al.

Page 1 of 1

It is certified that error appears in the above-identified patent and that said Letters Patent is hereby corrected as shown below:

In the Claims

Column 6 Claim 9, Line 67 "signal," should be deleted

Signed and Sealed this
Twenty-sixth Day of December, 2023

Katherine Kelly Vidal
*Director of the United States Patent and Trademark Office*